United States Patent [19]

Share

[11] Patent Number: 4,852,587
[45] Date of Patent: Aug. 1, 1989

[54] PROTECTIVE SHIELD AND RESTRAINING DEVICE

[76] Inventor: Mark Share, 2401 NE. 187th St., Miami Beach, Fla. 33180

[21] Appl. No.: 145,398

[22] Filed: Jan. 19, 1988

[51] Int. Cl.$^4$ ............................................. A61F 13/00
[52] U.S. Cl. ................................... 128/869; 128/870; 128/873
[58] Field of Search .................... 128/133, 134, 89 R, 128/869, 870, 871, 873, 874, 876; 297/464, 465; 5/82 R, 89, 444, 494

[56] References Cited

U.S. PATENT DOCUMENTS

| | | | |
|---|---|---|---|
| 2,313,337 | 3/1943 | Gurke | 128/134 |
| 2,455,884 | 12/1948 | Steigerwald | 128/134 |
| 2,664,083 | 12/1953 | Heymans | 128/134 |
| 2,766,751 | 10/1956 | Topa | 128/134 |
| 2,899,692 | 8/1959 | Finken | 5/82 |
| 2,948,278 | 8/1960 | Topa | 128/134 |
| 3,315,671 | 4/1967 | Creelman | 128/134 |
| 3,399,670 | 9/1968 | Veasey | 128/134 |
| 3,986,505 | 10/1976 | Power | 5/89 |
| 4,299,211 | 11/1981 | Doynow | 128/89 R |

Primary Examiner—Robert A. Hafer
Assistant Examiner—Michael Brown
Attorney, Agent, or Firm—John H. Faro

[57] ABSTRACT

A device for subduing and then restraining a violent person comprising a relatively-stiff, bendable shield having opposed major surfaces. One of the major surfaces, designated the back surface, has attached thereto at least two handles, at least one strap, and means for releasably fastening the strap to the back surface.

8 Claims, 2 Drawing Sheets

PROTECTIVE SHIELD AND RESTRAINING DEVICE

BACKGROUND OF THE INVENTION

1. Field of the Invention

This invention relates to a novel device for subduing and then restraining a violent person while, at the same time shielding others from possible injury from that violence. The novel device is suitable for use by medical personnel, law enforcement officers, prison guards and paramedics.

2. Description of the Prior Art

Various devices for restraining a person who is temporarily violent have been described previously, for example, in U.S. Pat. Nos.:

2,664,083 to J. A. Heymans,
2,940,443 to E. S. Baker,
4,117,840 to R. A. Rasure,
4,119,095 to M. Lewis,
4,299,211 to D. Doynow,
4,571,000 to O. S. Holder and
4,685,454 to J. T. Posey.

All of the devices described in the foregoing patents are garments of one type or another, with or without sleeves, that can restrain a violent person after it has been donned on that person. However, before the device has been put on, that person may be kicking, punching, biting, throwing things, etc. to prevent being subdued and restrained. It is ordinarily the practice for one or more people to physically overpower the violent person while, at the same time, hazarding injury from the violence. These prior devices do not provide any protection to the restrainer while the violent person is being restrained. Also, these prior devices do not provide a carrier for transporting the person after being restrained.

OBJECTS OF THE INVENTION

An object of this invention is to provide a novel device for subduing and restraining a violent person.

Another object is to provide a novel device which may be readily placed in position to subdue a violent person and, at the same time, protect other persons from the violence.

Still another object is to provide a novel device which requires a minimum of force to be used to subdue and then restrain a violent person.

A further object is to provide a novel device of the type described which s relatively light in weight, easy to carry and apply, effective in operation and relatively low in cost.

A still further object is to provide a novel device of the type described which does not require the arms or head of a violent person to pass through an opening or into a sleeve of the device.

Yet another object is to provide a novel restraining device which is also a carrier for transporting a person after being restrained.

SUMMARY OF THE INVENTION

The novel device for subduing and then restraining a violent person comprises a relatively-stiff, bendable shield having opposed major surfaces. One of the major surfaces has, attached thereto, at least two spaced handles, at least one strap and means for fastening the strap to the one major surface. In a preferred embodiment, the shield has a multi-layer construction including two outer water-repellant layers and a layer of padding therebetween. The device may include means to facilitate the bending of the shield in its lateral or transverse direction. Preferably, the novel device has four straps, and the fastening means are hook-and-pile fasteners.

To use the device, one or more subduers hold the shield in front of them by its handles and advance until the shield contacts the violent person. The shield provides substantial protection against injury that can result from such violence as kicking, punching, biting, missles, etc. Upon contact, the shield is wrapped around the violent person, enveloping the persons legs and arms, in a manner similar to wrapping a blanket around a person. At that point, the strap or straps are releasably fastened so as to hold temporarily together the lateral edges of the shield. Thereby, a minimum of force is used to subdue and restrain the person, and the shield with its padding protects all parties from serious injury. The novel device is light in weight, easy to carry and apply, effective in operation and relatively low in cost.

As an additional feature, the novel device can be used as a carrier for the subdued person, particularly by the placement of the handles in positions on the shield which are at the sides when the shield is encompassing the subdued person. It is noteworthy that neither the arms nor the head of the person needs to pass through an opening or sleeve of the novel device in order to be effective, as in prior restraining devices.

DETAILED DESCRIPTION OF THE INVENTION INCLUDING PREFERRED EMBODIMENTS

Figure 1:
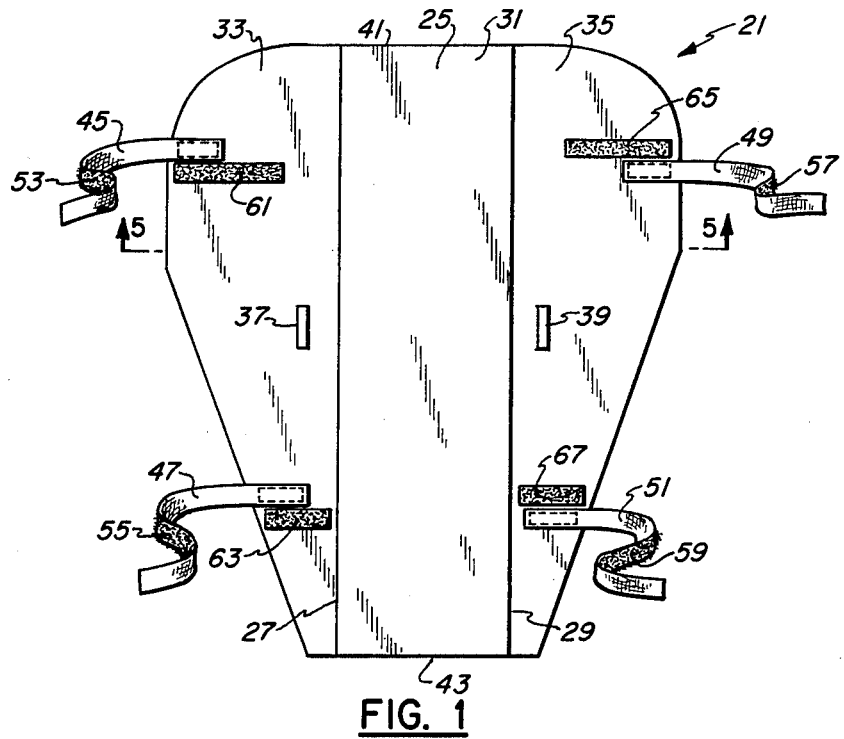
FIG. 1 is a rear elevational view of a preferred embodiment of the novel device.

The following description of some of the preferred embodiments of the concepts of this invention is made in reference to the accompanying figures. Where an individual structural element is depicted in more than one figure, it is assigned a common reference numeral for simplification of identification and understanding.

Figure 5:
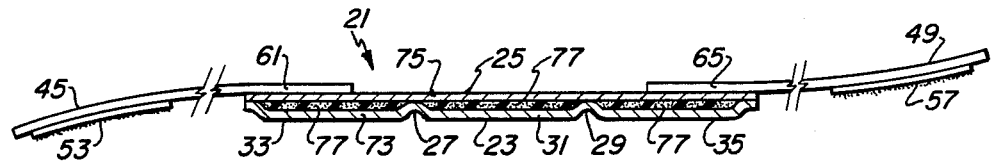
FIG. 5 is a sectional view of the device shown in FIG. 1 viewed along section line 5–5.

The preferred embodiment of the novel device shown in FIGS. 1 and 5 comprises a relatively-stiff, bendable shield (21) having a major front surface (23) and an opposed major back surface (25). The shield (21) is of such size as to be capable of bending around a person to be restrained and to cover the torso, arms and legs of that person. The shield (21) shown in FIG. 1 is about 62 inches high and about 54 inches at its widest point. As shown in FIG. 1, the shield (21) includes means to facilitate the bending of the shield in the lateral direction. To this end, the shield (21) is constructed with two spaced, substantially-parallel, elongated regions (27) and (29) which are thin relative to the adjacent portions of the shield. The right and left elongated depressions (27) and (29) essentially divide the shield into a central panel (31), a contiguous right side panel (33), and a contiguous left side panel (35) respectively.

Attached to the back surface (25) are a right handle (37) and a left handle (39) in the right and left panels (33) and (35) respectively about midway between the top edge (41) and the bottom edge (43) of the shield (21). Two cloth right straps (45) and (47) are attached to the right panel (33), spaced above and below the right handle (37). Two cloth left straps (49) and (51) are attached to the left panel (39). The straps (45), (47), (49) and (51) extend sidewardly and each strap has one of a pair of hook-and pile fasteners (53), (55), (57) and (59) respectively attached to the front surface thereof. The mating fastener (61), (63), (65) and (67) for hook-and-pile fastener (53), (55), (57) and (59) respectively is attached to a similar position on the opposite side panel. Hook-and-pile fasteners are sold commercially under the trademark "VELCRO", and are available in different sizes in mating pairs.

The novel shield (21) may be used by a singular subduer by holding both handles (37) and (39) with the shield in front and advancing until the shield contacts the person to be subdued. At that point in time, the subduer slides his arms around the shield (21) so as to wrap it around the person to be subdued, thereby enveloping the arms and legs of the person to be subdued. All the while, the shield (21) protects the subduer from injury due to any violence. The subduer with his arms around the person now fastens the upper straps (45) and (49) with the fasteners (53) to (65) and (57) to (61) respectively. Then, the lower straps (47) and (51) are releasably fastened with the fasteners (55) to (67) and (59) to (63) respectively. Alternatively, two subduers can use the novel shield (21), whereby each subduer holds a handle and the edge of a side panel (33) and (35). Following a similar procedure to that described above, the shield is bent around the person to be subdued and the straps fastened as described.

Figure 2:
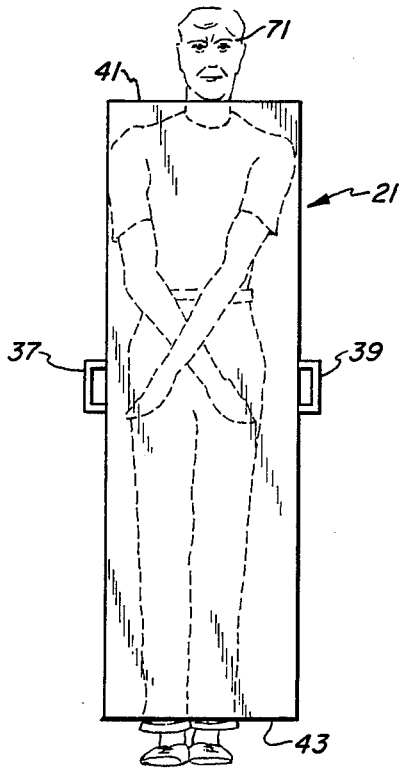
FIGS. 2 and 3 are, respectively, rear and front views of the device shown in FIG. 1 wrapped and fastened around a restrained person in an upright position.
Figure 3:
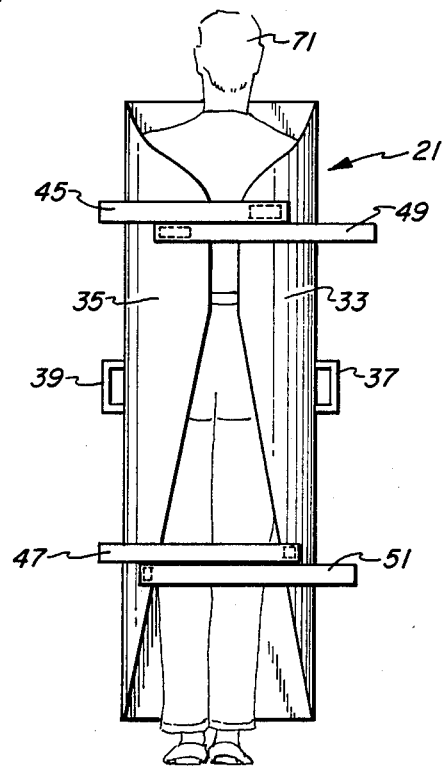
Figure 4:
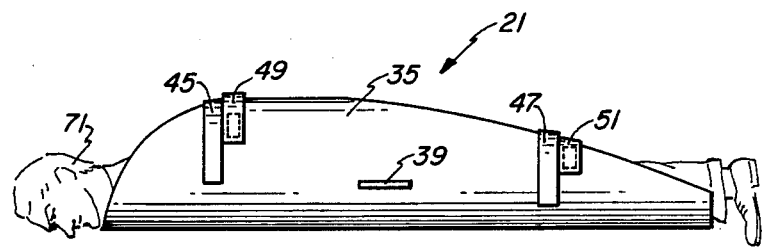
FIG. 4 is a side elevational view of the combination shown in FIGS. 2 and 3 rotated so that the novel device is used as a carrier for transporting the subdued person in a prone position.

FIGS. 2 and 3 show the shield (21) wrapped around a subdued person (71) viewed from the back and front sides of the shield (21) respectively. Although that persons arms and legs are limited in their movement, the restrained person can see what is going on, can talk, etc. without injury to himself or to others. The constraint on movement of his legs is, however, significant in that he cannot run or charge his subduers. It is noteworthy that the shield is not specific in design for use with males or females or to the type of clothing that is worn. FIG. 4 shows the combination shown in FIGS. 2 and 3 but rotated about 90° to show the use of the shield (21) as a carrier for the subdued person (71). The handles (37) and (39) are positioned in the side panels (33) and (35) to aid in using the shield (21) as a carrier. The restrained person can be freed easily from the novel device simply by releasing the fasteners.

The shield (21) is preferably constructed, as shown in FIG. 5, of two outer layers (73) and (75) of water-repellant, sheet-like material such as a vinyl plastic sheet or a vinyl-coated cloth. There is at least one inner layer of padding (77) between the outer layers (73) and (75) in each of the panels (31), (33) and (35). A preferred padding (77) is a foam plastic, such as polyurethane foam. The stiffness and bendability of the shield (21) is imparted by the materials chosen. Bendability is imparted by the materials chosen. Bendability is most important in the lateral direction and greater stiffness is desirable in the longitudinal direction. Thus, in the preferred embodiment the shield is relatively stiff with increased bendability imparted with two or more elongated, longitudinal depressions (27, 29) that are thinner than the adjacent portions of the shield (21). A stiffener layer (not shown) adjacent to the padding (77) may be desirable, particularly in the central panel (31). The straps (45), (47), (49) and (51) are preferably made of canvas.

Figure 6:
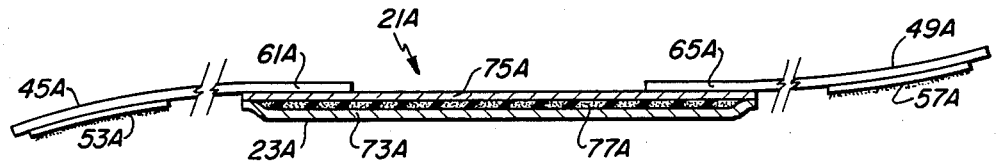
FIGS. 6 and 7 are sectional views of alternative structures of the novel device similar to the view in FIG. 5.
Figure 7:
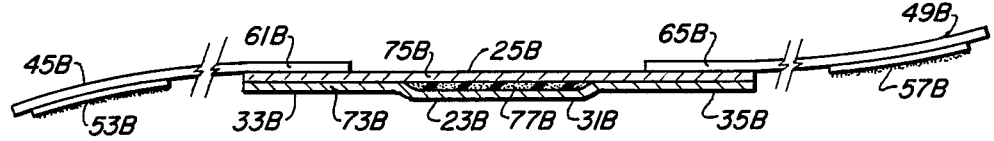

The novel shield (21) may have other shapes, sizes and constructions. For example, as shown in FIG. 6, the shield (21A) may be constructed of a single bendable panel with no elongated depressions therein. As another example shown in FIG. 7, the padding (77B) may be present in only the central panel (31B), and the side panels (33B) and (35B) are both thinner and more bendable than the central panel (31B). In the embodiment shown in FIG. 7, it may be desirable to include a bendable stiffener, such as a layer of buckram (not shown) in the side panels (33B) and (35B). The combination of the compliancy of the outer layers (73) and (75), the resiliency of the padding (77) and the bendability of the shield (21) all contribute to preventing injury such as bruising, laceration, etc., to the restrained person (71).

The foregoing figures and descriptions thereof are provided as illustrative of some of the preferred embodiments of the concepts of this invention. While these embodiments represent what is regarded as the best mode for practicing this invention, they are not intended as delineating the scope of the invention, which is set forth in the following claims.

What is claimed is:

1. A device for subduing and then restraining a violent person comprising a shield having opposed major surfaces, a longitudinal direction terminating in a top edge and a bottom edge and a lateral direction terminating in side edges, said shield including two narrow, substantially-parallel, bendable regions of reduced thickness extending in said longitudinal direction, a wide stiff central panel between said bendable regions, and a wide stiff side panel attached at one side thereof to each of said bendable regions and terminating on its other side in one of said side edges, whereby said shield is bendable in said lateral direction to fit around said person, at least two handles for manually supporting and manipulating said shield attached to one of said major surfaces, one of said handles being attached to each of said side panels, at least one strap attached at one end thereof to said one major surface and fastening means for releasably attaching the extended portion of said strap to said one major surface.

2. The device defined in claim 1 wherein each panel of said shield has a multi-layer construction including two outer layers of water-repellant sheet-like material and at least one inner layer of padding between said outer layers.

3. The device defined in claim 1 wherein said padding is an elastic plastic foam.

4. The device defined in claim 1 including two straps attached to said one major surface adjacent to each of said side edges and extending beyond said side edges in a substantially lateral direction, and fastening means adapted to releasably fasten each said strap to said one major surface.

5. The device defined in claim 4 wherein each fastening means includes a mating pair of hook-and-pile fasteners, one of said pair being fixedly attached to a strap and the other of said pair being fixedly attached to said one major surface.

6. The device defined in claim 1 wherein said fastening means are mating pairs of hook-and-pile fasteners.

7. The device defined in claim 1 including four cloth straps attached to said one major surface of said shield and a strap fastener attached to each of said straps, said shield having a mating shield fastener positioned on said one major surface for joining to each of said strap fasteners.

8. The device defined in claim 1 wherein said major surfaces are water-repellant and compliant, and including a layer of elastic foam padding between major surfaces.

* * * * *